United States Patent [19]

Rosen et al.

[11] Patent Number: 4,845,729
[45] Date of Patent: Jul. 4, 1989

[54] METHOD AND APPARATUS FOR DIAGNOSIS OF LEAD TOXICITY

[75] Inventors: John F. Rosen, Riverside, Conn.; Daniel N. Slatkin, Bayside; Lucian Wielopolski, Shirley, both of N.Y.

[73] Assignee: Elex Analytical Technologies Corp., Upton, N.Y.

[21] Appl. No.: 158,495

[22] Filed: Feb. 22, 1988

[51] Int. Cl.$^4$ .......................................... G01N 23/223
[52] U.S. Cl. ........................................ 378/45; 378/44; 378/49
[58] Field of Search ........................ 378/44, 45, 47, 49

[56] References Cited

U.S. PATENT DOCUMENTS 4,417,355 11/1983 Anisovich et al. .................... 378/83

OTHER PUBLICATIONS

Wielopolski et al., "Feasibility of Noninvasive Analysis of Lead in the Human Tibia by Soft X-Ray Fluorescence," *Med. Phys.*, 10(2), pp. 248-251, Mar. 1983.
Wielopolski et al., "In Vivo Bone Lead Measurements: A Rapid Monitoring Method for Cumulative Lead Exposure," *Am. J. Of Ind. Medicine*, 9: 221-226, 1986.
Christofferson et al., "Polarized X-Ray in XRF-Analysis for Improved in Vivo Detectability of Cadmium in Man," *Phys. Med. Biol.* 28, No. 10, pp. 1135-1144, 1983.
"Preventing Lead Poisoning in Young Children," Centers for Disease Control (1985).
Horowitz et al., *The Art of Electronics*, Sect. 14.07 (1980).
Torok et al., "Heterogeneity Effects in Direct X-Ray Fluorescence of Hair", *X-Ray Spectrometry*, 13 No. 1, pp. 27-32 (1984).
Wobrauschek et al., "X-Ray Fluorescence Analysis with a Linear Polarized Beam after Bragg Reflection from a Flat or a Curved Single Crystal," *X-Ray Spectrometry*, 12, No. 2, pp. 72-78 (1983).
"Chemical Effects in X-Ray Fluorescence Analysis," Kateria et al. *X-Ray Spectrometry*, 15, pp. 49-53 (1986).
Kikkert, "X-Ray Fluorescence Sees Light Elements," *Research and Development*, pp. 82-86, Feb. 1986.
Wielopolski et al., "Feasibility Study for the in Vivo Measurement of Lead in Bone Using L-X-Ray Fluorescence," *IEEE Trans. on Nuclear Science, NS-28:* 114 (1981).
"Non-Invasive Detection of Tibial Bone Lead in Intact Legs by L X-Ray Fluorescence", *Toxicologist*7:77, Wielopolski, Feb. 1987.
"L-X-Ray Fluorescence Measurements of Cortical Boned Lead in Lead-Toxic Children" Rosen et al., May 1988.
"L-X-Ray Fluorescence: A Rapid Assessment of Cortical Bone Lead in Pb-Toxic Children" Rosen et al., *Pediatric Research 21:* 287A (May 1987).
"L-X-Ray Fluorescence: A Rapid Assessment of Cortical Bone Lead in Pb-Toxic Children", Rosen et al., Feb. 1988.
Kneip et al., "Isotape Exited X-Ray Fluorescence", *Analytical Chemistry*, vol. 44, No. 14, pp. 57A-68A, Dec. 1972.
"Three I-R 100 Awards for BNL", *Brookhaven Bulletin*, pp. 1-2, Sep. 18, 1987.

(List continued on next page.)

*Primary Examiner*—Janice A. Howell
*Assistant Examiner*—David P. Porta
*Attorney, Agent, or Firm*—Pennie & Edmonds

[57] ABSTRACT

Improved methods and apparatus for in vivo measurement of the skeletal lead burden of a patient and for diagnosis of lead toxicity are disclosed. The apparatus comprises an x-ray tube emitting soft low energy x-rays from a silver anode, a polarizer for polarizing the emitted x-rays, and a detector for detecting photons fluoresced from atoms in the patient's tibia upon irradiation by the polarized x-rays. The fluoresced photons are spectrally analyzed to determine their energy distribution. Peaks indicating the presence of lead are identified if the patient has relatively high bone lead content. The data may be compared to data recorded with respect to a similar test performed on patients having also had the conventional EDTA chelation tests performed thereon in order to correlate the test results with respect to a particular patient to the conventionally accepted EDTA chelation test.

14 Claims, 4 Drawing Sheets

OTHER PUBLICATIONS

"Montefiore's High Tech War Against Silent Disease", *Monitor*, pp. 1,3,4,7, and 16, Aug. 1987.

"Guarding Against Lead", *Newsweek*, p. 3, Oct. 1987.

"1987 I-R 100 Competition Winners", *Research and Development*, p. 64, Oct. 1987.

"Scientist Invents Instruments to Detect Lead in Kids", Undated, Pinkham.

"Ionizing Radiation Exposure", *RRS News*, pp. 1–8, Mar. 1988.

Ahlgren et al., "An X-Ray Fluorescence Technique for in Vivo Determination of Lead Concentration in a Bone Matrix", *Phys. Med. Biol.*, 24, No. 1, pp. 136–145, 1979.

Fig. 1

XRF SPECTRA FROM PRE-SCHOOL CHILDREN

METHOD AND APPARATUS FOR DIAGNOSIS OF LEAD TOXICITY

GOVERNMENT RIGHTS

The U.S. Government has rights in this invention pursuant to Contract No. DE-AC02-76CH0016 awarded by the U.S. Department of Energy.

FIELD OF THE INVENTION

This invention relates to methods and apparatus for diagnosis of lead toxicity in humans. More particularly, the invention relates to a method for the direct and non-invasive in vivo measurement of the actual lead content of bones of humans, where 75-95% of lead in humans is found. This non-invasive quantitative test can be performed in an essentially safe and high speed fashion, and yields results which correlate highly to previous tests which are much more expensive, more cumbersome, less definitive, and painful to perform. The invention further includes methods of diagnosis and treatment based on such tests.

BACKGROUND AND SUMMARY OF THE INVENTION

The hazards posed to health by excessive exposure to lead are well documented In children, exposure to lead can cause growth deficiencies, loss of intelligence, hyperactivity and other serious problems. These matters are well documented in the medical literature. Lead is also well known to be toxic to adults.

Lead toxicity remains a substantial health problem, despite recent efforts to reduce the amount of lead in the environment, particularly in the United States, by use of low-lead gasolines and otherwise. The treatments which are available to remove lead from the body are relatively complex and expensive. Accordingly a rapid, reliable and definitive test for determining which patients require in-hospital treatment is important.

More particularly, it is currently estimated by the Federal Centers for Disease Control (CDC) that between 2 and 3 million children in the United States may suffer from lead toxicity. "Lead toxicity" is currently defined by the CDC as either (a) a blood lead content above 55 micrograms per deciliter of whole blood, associated with an "elevated" erythrocyte protoporphyrin (EP) concentration of 35 micrograms/deciliter or greater, or (b) an "elevated" blood lead level of 25-55 micrograms/deciliter, together with an elevated EP level, again of 35 micrograms/deciliter.

In case (a) above, treatment using a calcium disodium ($CaNa_2$) EDTA chelator is normally initiated immediately upon detection of lead toxicity as thus defined, that is, simply responsive to the results of a blood test.

In case (b), a further soft tissue and skeletal lead burden test involving an EDTA chelator, discussed in detail below, is normally performed. Based on the results of this latter test, similar treatment may be initiated.

The blood lead test reflects recent exposure only, and only measures lead concentration in blood. Indices of adverse effects of lead on humans have also been recognized at blood lead levels below 25 micrograms/deciliter. The EP test is an index of lead toxicity on hemoglobin. Blood lead level—not EP values—primarily determines the sequence of diagnostic testing and subsequent treatment.

As indicated, both blood lead and EP tests are generally considered to reflect recent exposure to lead, e.g., in the past 30-90 days. A more serious problem is posed to health by the total body burden of lead, that is, the lead absorbed into the patient's tissues over his entire lifetime. This can only accurately be measured by direct evaluation of the lead content of the skeleton, in which a known proportion of the total lead absorbed by the body accumulates over time.

As indicated, a blood lead concentration in the 25 to 55 microgram/deciliter range is considered by the CDC to be "elevated". It is estimated that 2-3 million preschool children in the United States have blood lead levels in this range. Clearly, it is desirable to identify those having higher total lead burdens, so that they can be treated promptly, and so that treatment resources can be allocated efficiently and equitably. At present, the 25-55 microgram per deciliter range of blood lead contents is considered to be an inconclusive indicator of the necessity for treatment for lead toxicity, even when an "elevated" lead result is obtained. Accordingly, a further test, which accurately indicates the soft tissue and skeletal lead burden, is called for in these cases.

The current test for determining which children require treatment for lead toxicity is an "EDTA provocative" test, referred to herein as the "EDTA chelation" test. This test involves administering a painful injection of a chelating agent, the calcium disodium salt of ethylene diamine tetracetic acid (EDTA), which causes lead to be removed from the extracellular fluid and secondarily from bone and soft tissues and excreted. Performance of the test requires that all of the urine of the child be collected for a period of at least eight hours and in some cases up to 24 hours, so that the child must be monitored completely during that time. This is a relatively onerous test requirement, and the test is currently only available in a few hospitals and other medical facilities in the United States. Obviously, it is impractical to test millions of children by this cumbersome technique.

The present invention provides an improved test which is anticipated to obviate the present EDTA chelation test for most children, and which furthermore is responsive only to lead stored in bone.

Applicants and others have published a number of papers discussing the possibility of measuring skeletal lead burden in humans using x-ray fluorescence methods. Such techniques are used throughout science and industry. Broadly, in x-ray fluorescence analysis, a target of interest is irradiated by x-rays from a suitable source. Atoms in the target area absorb the x-rays and emit photons at a lower frequency, that is, fluoresce. The energies of the emitted photons are uniquely characteristic of the fluorescing atoms. The energy spectrum of the emitted photons can be analyzed using conventional instrumentation and used to determine the presence and relative amounts of the atoms making up the matter in the target area.

The present invention relates to improvements in methods and apparatus for performing such in vivo x-ray fluorescence tests to determine human skeletal lead burden and to methods of diagnosis and treatment based thereon.

For example, in "Feasibility of Non-Invasive Analysis of Lead in the Human Tibia by Soft X-ray Fluorescence," *Med. Phys.* 10(2), March/April 1983, pages 248-251, (the "1983 paper" hereinafter), applicants (with others) discuss a study assessing the feasibility of measuring bone lead by x-ray fluorescence as outlined above. In that study, a radioactive iodine source ($^{125}$I) was used as a source of "soft" x-rays, that is, low energy x-rays of 27.47 and 30.99 keV, which were used to irradiate the tibial cortex of the legs of six adults, post mortem. The results obtained by spectrum analysis of fluorescent photons correlated well to lead concentrations measured subsequently by flameless atomic absorption spectroscopy.

The 1983 paper suggests that use of relatively low energy soft x-rays to excite fluorescence would improve the safety of in vivo x-ray fluorescence lead measurements as compared to similar tests using higher energy hard x-rays (shown in, for example, Ahlgren et al., Phys. Med. Biol. 24, 136(1979)). The relatively low energy of the soft x-rays (approximately 10–30 keV) prevents them from penetrating deeply into the body tissues or from scattering beyond the body. This improves the safety of in vivo testing. Since the soft x-rays do not penetrate deeply into the body tissues, the bone to be thus examined must be near the surface of the patient's skin. Accordingly, the superficial tibial cortex, which is normally quite close to the surface, was explored. In the 1983 paper, the thickness of the overlying tissue was measured ultrasonically.

Applicants have subsequently measured the absorption of such soft x-rays in the soft tissue overlying the tibia and have developed a mathematical correction for the thickness of the overlying tissues on the absorption of the x-rays. See Wielopolski et al., "In Vivo Bone Lead Measurements; a Rapid Monitoring Method for Cumulative Lead Exposure", *American Journal of Industrial Medicine* 9, 221–226, 1986.

In the 1983 paper referred to above, applicants discuss the possibility of using an "x-ray machine" rather than a radioactive element, as follows:

If an x-ray machine rather than a $^{125}$I source were used to excite XRF [x-ray fluorescence], one could optimize the sensitivity of the system to detect lead, strontium or zinc in bone by varying the energy of the incident radiation. An --ray machine could also provide a sufficiently intense beam so that the polarization technique could be utilized. A polarized beam reduces the background and therefore improves the overall signal-to-noise ratio.

\* \* \*

A different source $^{109}$Cd which emits silver x-rays, can also be used for the fluorescence analysis of lead. It was found that with $^{109}$Cd the advantage of an increased photo electric cross-section in lead at the lower energies is offset by a lower conversion factor from x-ray flux to dose at these energies. One leg was analyzed with the $^{109}$Cd source . . . At present, there appears to be no clear advantage of one source over the other. (page 251).

Applicant's original 1983 paper discussed above was preceded by Wielopolski et al., "Feasibility Study for the In Vivo Measurement of Lead in Bone using L-x-ray Fluorescence," *IEEE Transactions on Nuclear Science*, Vol. NS-28, 114–116, 1981. The disclosure of this 1981 paper is included within that of the 1983 paper discussed in detail above.

Other references discussing x-ray fluorescence techniques generally indicate that the efficiency of the process depends upon the material from which the anode of the x-ray tube is constructed, and other factors. See Kikkert, "X-ray Fluorescence Sees Light Elements," *Research and Development*, February 1986, pages 82–86.

The present invention comprises methods and apparatus for measuring the skeletal lead burden in humans, especially children, and accompanying methods for diagnosis and treatment of lead toxicity. According to the present invention, a small area (2–4 centimeters square) of the frontal portion of the patient's leg, directly over the tibia, is exposed to soft x-rays from an x-ray tube comprising a silver anode. These x-rays undergo scattering and photoelectric absorption in lead and other atoms in the bone, which then fluoresce, emitting radiation of characteristic energies. A Si(Li) detector detects the fluorescent photons. A spectrum analyzer provides a plot of the energy of the fluorescent photons which can be readily analyzed automatically or by an operator to determine the presence and relative amount of lead in the bone.

Such x-ray fluorescence data from a particular patient can then be correlated with similar data obtained from previously tested patients, who had also been tested using the EDTA chelation test. This allows direct assessment of the extent of lead burden in the particular patient with respect to the recognized EDTA chelation test, without actually performing it. This fact enables a valid judgment to be made whether the patient should undergo chelation therapy. In this way, the results of the x-ray fluorescence test of the invention are directly comparable to those from the EDTA chelation test, and diagnosis and treatment can be performed accordingly.

More particularly, and according to an important aspect of the invention, the x-ray fluorescence test of the invention in combination with the conventional blood lead test provides a complete testing methodology for measurement of body burden of lead. EDTA chelation testing is eliminated; EP testing is employed as a pre-screening method, if at all.

The effective equivalent radiation dose actually absorbed by the patient in a test performed according to the invention is substantially less than that absorbed in a single dental x-ray. Moreover, the relatively "soft", i.e., low energy, x-rays employed according to the invention are highly localized and do not penetrate into the patient's tissues to any significant degree, such that the danger posed by the exposure is greatly minimized. Further, the use of soft x-rays also minimizes the need for elaborate shielding or inconvenient safety precautions for the personnel administering the tests. In fact, the mother can safely remain near the child during the test; this is not permissible if hard x-rays are used.

In the preferred embodiment, the radiation is polarized by passing it through a generally conventional polarizing device prior to being incident on the tibia of the patient; this improves the signal-to-noise ratio of the detected signal as it reduces reflection of the incident radiation directly onto the detector.

BRIEF DESCRIPTION OF THE DRAWINGS

The invention will be better understood if reference is made to the accompanying drawings, in which.

DESCRIPTION OF THE PREFERRED EMBODIMENTS

The overwhelming majority of children who are diagnosed as lead toxic (as that term is determined by the CDC) have blood lead contents of between 25–55 micrograms/deciliter. A much smaller number have blood lead levels exceeding 55 micrograms/deciliter. These patients can normally be effectively treated by chelation and subsequent removal from the source of lead. To determine which require chelation or other lead-excreting treatment, the so-called EDTA chelation test is now conventionally employed.

According to this test, an injection of a chelating drug is given to the patient and all urine is collected for a period of time, i.e., eight hours in the case of children. The chelator causes lead to be excreted, primarily from the extracellular fluid and secondarily from the bone and soft tissues. The lead is collected in the urine, such that the amount of lead in the urine provides a quantitative measure of the amount of lead present in the soft and hard tissues. However, the test is extremely cumbersome and painful to administer and in fact is now only available at a few locations across the United States.

This methodology is accordingly unsuitable for determining which of the estimated 2–3 million children in the United States who have elevated blood levels require treatment for lead toxicity.

Any test which is to be applicable to diagnosis of such a large number of patients must be inexpensive and rapidly and reliably administered. Such a test must not expose the patient to unreasonable risk from radiation and should be essentially painless, minimally inconvenient, and require little or no skill to interpret the results of the test.

These objects of the invention are met by the present invention, which comprises a skeletal lead burden test which is safe and painless, which presently requires less than twenty minutes of the patient's time, and the results of which are readily interpretable by commercially available equipment.

Figure 1:
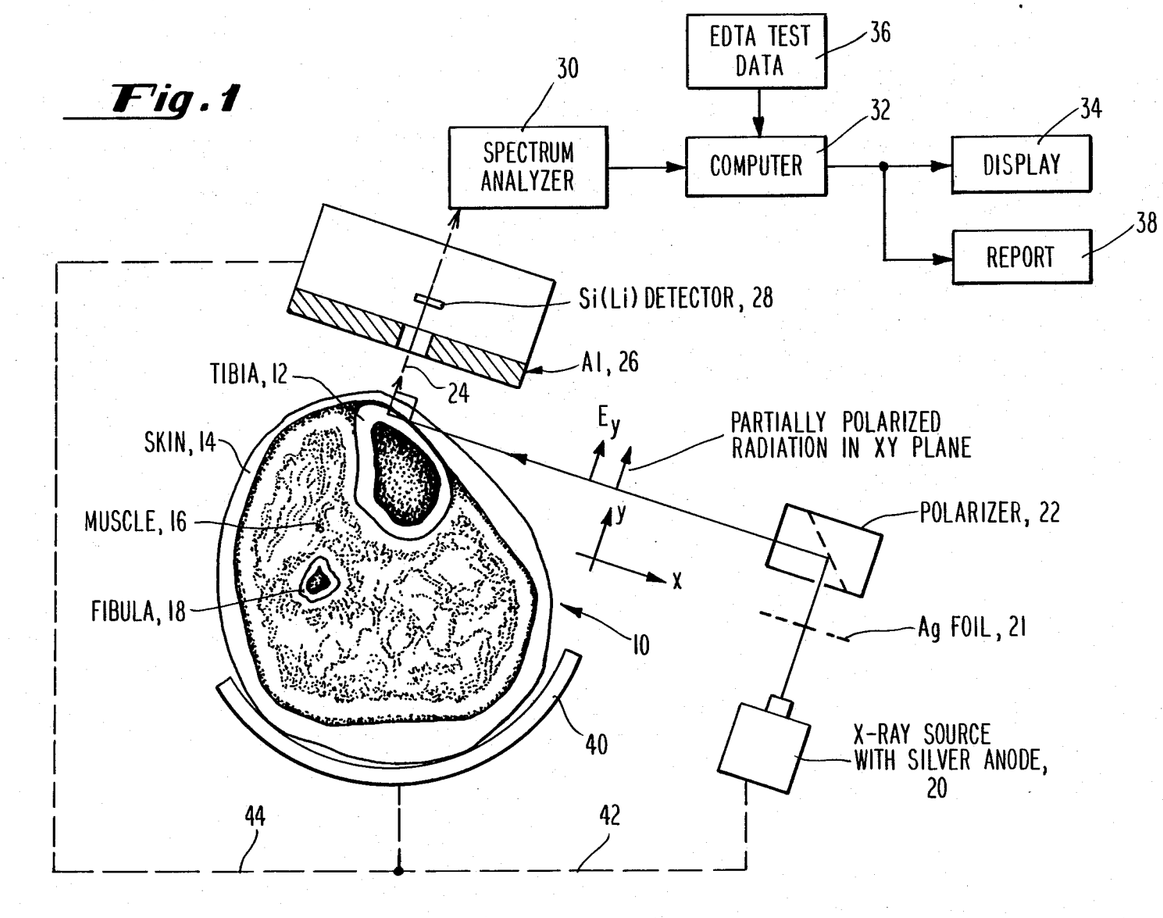
FIG. 1 shows a schematic view of the apparatus of the invention.

Referring now to FIG. 1, a schematic diagram of the apparatus of the invention is shown in conjunction with a cross-sectional view of a patient's leg. As indicated, leg 10 comprises the tibia 12 which is surrounded by the skin 14. Muscle tissue 16 separates the tibia 12 from the fibula 18. Near the frontal portion of the leg, the bone of the tibia is almost always between 3 and 8 millimeters from the surface of the skin 14, as measured by ultrasonic devices. Accordingly, even "soft", relatively low energy, x-rays penetrate through the skin 14 and are incident upon the tibia 12.

According to the invention, the leg 10 is strapped to a support member 40. The frontal portion of the tibia 12 is thereby in a defined relationship to a source 20 of x-rays and a detector 28 of fluorescent photons, which are fixedly connected to support member 40, as indicated at 42, 44. The alignment of the tibia 12 with respect to the source 20 and detector 28 is further discussed below.

According to the invention, relatively "soft," low-energy x-rays are provided by an x-ray source 20 with a silver anode, as indicated; the soft x-rays have energies in the 0–50 keV range. More specifically, the silver anode emits x-rays at 22.16 and 24.94 keV. These x-rays pass through a polarizer 22 which polarizes them substantially into the X-Y plane as shown in FIG. 1. A silver foil member 21 may be disposed between the source 20 and the polarizer 22; this foil serves as a bandpass filter for silver x-rays emitted from the anode, and thus reduces the so-called "bremhsstrahlung" radiation from the x-ray tube.

The polarized x-rays are incident on the bone of the tibia 12 as indicated, and some fraction of them excite atoms in the bone, by creating vacancies in the inner atomic shells of lead and other atoms bound to the bone. When electrons drop into these vacancies in the lower atomic shells, they emit photons the energies of which are characteristic of the excited atoms. Some of the emitted or "fluorescent" photons travel along a path 24 at right angles to the path of the incident polarized x-rays, pass through a hole in an aluminum shield 26, and are incident on a conventional Si(Li) detector 28.

The detector 28 emits a signal responsive to each photon incident thereon, which is proportional to the energy of the incident photon. Operation of such detectors and analysis of the signals provided is well understood; see Horowitz and Hill, *The Art of Electronics*, sect. 14.07 (1980). In the preferred embodiment, the signal from the detector 28 is analyzed by a spectrum analyzer 30. The detector 28 provides output pulses of energy proportional to the energies of individual fluorescent photons. The spectrum analyzer measures the energy of the individual pulses, and uses this measurement to maintain a count of the number of photons received over time in each of a large number of energy "windows," e.g., 50 eV wide. The fluorescent photons are thus analyzed by their energy. Because the energy of the fluoresced photons is characteristic of the atoms emitting them, the counts accumulated by the spectrum analyzer can be used to directly identify and quantify the atoms.

Thus, after a predetermined exposure time has passed, typically on the order of 5 to 16.5 minutes depending on the intensity of the incident radiation, the results from the spectrum analyzer 30 may be processed by a computer 32 and employed, for example, to plot a spectrum as indicated at 34. Such a spectrum is shown and discussed below in connection with FIG. 2. Analysis of peaks in the data indicating the presence of lead can be performed by an operator or automatically, as discussed below.

More specifically, applicants have accumulated data from a number of patients on whom both the x-ray fluorescence test according to the invention and the CDC-approved EDTA chelation test have been performed. Data generated using the apparatus of FIG. 1 according to the invention is very highly correlated with data generated using the generally accepted EDTA chelation test discussed above. Results according to the invention can thus be employed directly to generate a diagnosis or other report 38 on the patient's condition, which is fully correlated to the EDTA test and hence to the CDC standards, as indicated generally at 36.

Figure 2A:
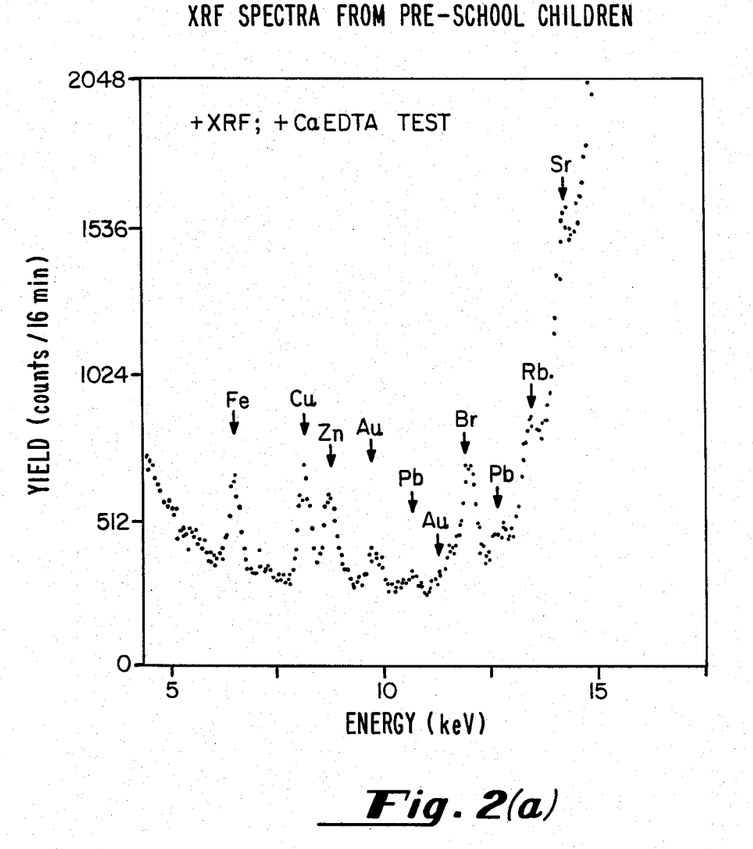
FIG. 2 shows exemplary plots of data detected in operation of the apparatus of the invention.
Figure 2B:
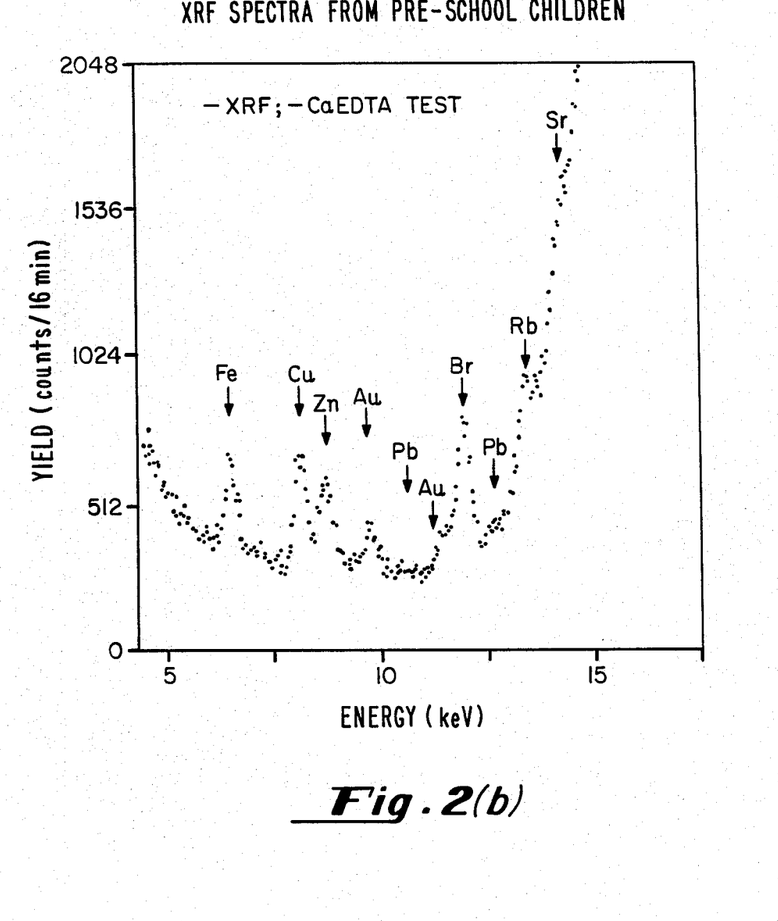

FIG. 2 shows typical results derived from tests on two children performed according to the invention as described above. FIG. 2 comprises two plots (FIGS. 2(a) and 2(b)), each representing the energy of the fluorescent photons in keV versus the number of photons detected in each of the energy windows with respect to one of the patients. The dots shown are the accumulated data output by each channel of the spectrum analyzer. The highest dot in each of the columns thus shows the total number of emitted photons accumulated in each energy window during a 16.5 minute exposure, versus the energy of the emitted photons. The peaks which appear thus indicate the presence of atoms of certain elements in the irradiated region.

Both patients were also tested using the CDC-accepted EDTA chelation test. As indicated by the legend in the upper left hand corner of FIG. 2, the upper curve, FIG. 2(a), is an x-ray fluorescence spectrum derived upon testing a patient who responded positively to the conventional EDTA chelation test. FIG. 2(b) is a comparable test derived upon testing a patient who responded negatively to the EDTA test.

More specifically, the children whose x-ray fluorescence tests according to the invention yielded the results shown in FIGS. 2(a) and 2(b) were both considered lead toxic based on the results of blood lead and EP tests; that is, both exhibited blood lead levels in the 25-55 microgram/deciliter range and elevated EP levels. Contemporaneous tests using the conventional EDTA chelation test as approved and accepted by the Federal Centers for Disease Control were then performed. The results indicated that child of FIG. 2(a) required in hospital chelation treatment, while the child of FIG. 2(b), even though this child was Pb-toxic, as noted, had a negative EDTA test result. Hence the child of FIG. 2(b) would not have been so treated under current guidelines.

The two curves shown in FIG. 2 each display certain peaks which have been marked to indicate the presence of the corresponding elements. For example, peaks for iron (Fe), copper (Cu), zinc (Zn), gold (Au), bromine (Br), rubidium (Rb), and strontium (Sr) appear in both curves. However, in the upper curve, FIG. 2(a), two peaks for lead (Pb) also appear and are marked. As can be seen from FIG. 2(a), these are readily discriminable by eye and appear at characteristic locations corresponding to emitted photon energies of approximately 10.55 keV and 12.61 keV. These are referred to in the literature respectively as "L-alpha" and "L-beta" peaks. The term "L x-ray fluorescence" is sometimes used to describe this phenomenon. In FIG. 2(b), the characteristic lead peaks do not appear; to the extent there may be some slight response in the characteristic lead energy regions, these are considered to be below the threshold for toxicity.

Spectra generated in x-ray fluorescence testing according to the invention, as shown in FIG. 2, have now been correlated with results from EDTA chelation tests from a sufficient number of patients that highly reliable conclusions as to lead toxicity can be reached by analysis of data generated using the x-ray fluorescence methods and apparatus of the invention. It is anticipated that the x-ray fluorescence test technique of the invention, together with the blood lead test as presently used, and the apparatus for its performance, will shortly become the CDC-accepted diagnostic technique and equipment for diagnostic definition and determination of "elevated body burden of lead requiring treatment" in humans, especially children.

It is also anticipated that the diagnosis process will shortly be automated to the extent that an operator does not have to interpret the display 34. Instead, the computer 32 will simply output a figure indicative of the lead burden of the patient, typically in micrograms of lead per gram of bone. The decision to prescribe chelation or other therapy can then rapidly be made by a physician. Such automatic diagnostic indication is considered to be within the scope of this invention.

More specifically, laboratory data analysis software is now available which is suitable for analyzing the data provided by the spectrum analyzer employed as shown in FIG. 1. The analysis essentially simply involves subtracting a value for the background (indicated by the overall U-shaped curve in FIG. 2) from the signal levels in the windows of the spectral analysis corresponding to lead fluorescence. Automation of such analysis is within the skill of the art.

Similarly within the skill of the art is comparison of skeletal lead burden data derived according to the invention with data similarly derived with respect to patients having also had the EDTA chelation test performed thereon, and suitable correlation of the results. This yields a diagnosis which is responsive to x-ray fluorescence data gathered rapidly, conveniently, and painlessly, according to the invention, but which is fully and accurately correlated to the CDC-approved EDTA chelation test.

Figure 3:
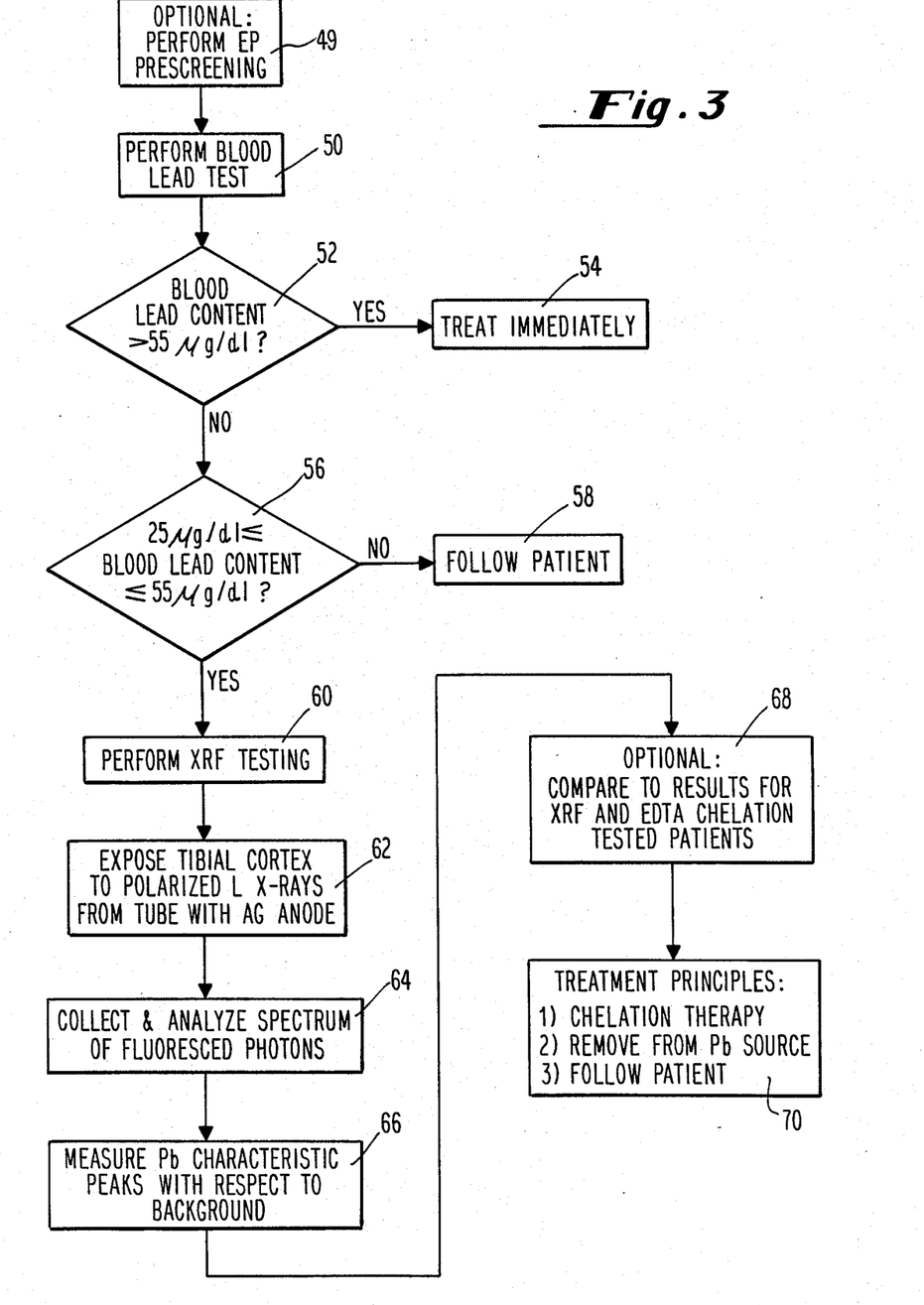
FIG. 3 shows the steps in diagnosis and treatment according to the invention.

FIG. 3 shows schematically the steps in diagnosis and treatment of lead toxicity in children according to the invention. Typically the process will begin after screening e.g. using the EP test, as indicated at 49. The process begins at 50 by performance of a conventional blood lead test. If the blood lead content is greater than 55 micrograms per deciliter, as tested at 52, the child is treated immediately with EDTA chelation therapy, as indicated at 54. If not, the blood lead content is still considered to be "elevated" if it is between 25 and 55 micrograms per deciliter, as indicated at 56. [The range of 25-55 micrograms/deciliter lead in blood mentioned herein is currently considered to be "elevated" by the CDC. In the future these values may be varied. Should this occur, the same diagnostic process using blood lead testing and x-ray fluorescence testing according to the invention would still be used and would still eliminate the EDTA chelation test.] If the blood lead content is less than 25 micrograms/deciliter, the child is followed as indicated at 58. That is, the child is seen again or tested further, to determine the cause for the elevated EP level detected at 49, and for treatment accordingly.

If the blood level content tested at 56 is within the 25-55microgram/deciliter range, x-ray fluorescence (XRF) testing is performed according to the invention, as indicated at 60. This begins at 62 by exposure of the frontal portion of the tibia to polarized soft x-rays from a tube with a silver anode, as discussed in detail above. At 64, the photons fluoresced by atoms in the bone of the tibia are collected and their spectrum is analyzed. At 66, the lead characteristic peaks are measured with respect to the background. This step can be performed visually by an operator or automatically, in both cases with the assistance of the multichannel analyzer. As discussed above, automation of this process is a straightforward matter which is well within the skill of the art. Essentially one need simply subtract the background radiation level surrounding the peaks characteristic of lead from the height of the peaks. The net difference indicates the height of the peaks.

According to the invention, the result, that is, the area of the peaks, whether determined automatically or by visual inspection, may then be compared at 68 to similar results generated by x-ray fluorescence testing according to the invention on patients who were also contemporaneously tested using the CDC-approved EDTA chelation test. This can be done by comparing the curve generated with respect to the particular patient to typical curves, as shown in FIG. 2(a) and FIG.

2(b). If the lead-characteristic peaks measured for the present patient are comparable to peaks similarly measured for previously tested patients who were diagnosed as requiring chelation therapy using the EDTA chelation test, it is presumed that the present patient requires the same treatment.

The foregoing paragraph describes direct correlation of x-ray fluorescence test results according to the invention to EDTA chelation test results. It is anticipated that this step will shortly become unnecessary as the CDC regulations and diagnostic practices are revised to employ the test of the invention. More particularly, according to the invention, x-ray fluorescence testing will be performed on patients whose blood lead levels are in the 25-55 microgram/deciliter range. The area of the lead characteristic peaks will indicate directly when the child should be admitted to the hospital for chelation therapy.

Depending on the test results, several concurrent treatment options are outlined at 70. Patients whose lead-characteristic peaks appear as in FIG. 2(a) will be typically treated by EDTA chelation therapy. At the same time, the patient should be removed from the source of lead. If the test reveals an elevated lead burden, the patient should at minimum be removed from the source of lead. Discharge from the hospital to a safe environment is indicated after successful treatment using EDTA.

A further improvement can be made in determining the actual amount of lead in the bone by noting the absolute number of fluorescent photons emitted during a predetermined period of time. The same simple step can be used to measure other elements contained in the bone, as indicated by the spectra of FIG. 2(a) and 2(b). In both cases a correction must be made for the thickness of the tissues overlying the tibia. According to another aspect of the invention, this can be done by ultrasonically measuring the thickness of the tissues and noting that the half-penetration depth of fluorescent photons in soft tissue (that is, the depth at which half of the emitted photons are absorbed) is approximately 1.5 millimeters. See Wielopolski et al, in *American Journal of Industrial Medicine*, supra. Comparison of the results of a particular test with those from prior tests can also be used to provide an objective measure of the actual lead burden.

According to the invention, the total skin dose of radiation required for an effective measurement is no more than 1 rad. The effective absorbed dose to the patient's body, that is, the "effective dose equivalent", as that term is used in the art, is less than 5 microSieverts. This is substantially less than the radiation received in connection with a single dental x-ray, and is roughly equivalent to the average radiation received from natural sources during one day. By comparison, other work being done involving x-ray fluorescence measurements of bone lead, using hard x-rays causing higher-energy K x-rays to be fluoresced from the bone, involves effective dose equivalents of radiation typically an order of magnitude greater. According to the present invention, only soft, low energy x-rays are provided by the x-ray source 20 employing a silver anode. Accordingly, even this small amount of radiation is rapidly attenuated and will not reach the marrow of the tibia, such that it will have little effect on the health of those tissues. The same fact means that little or no radiation will be incident on health care personnel administering these tests, further simplifying their administration.

As indicated above, the detector and source can be aligned with the tibia simply by visual observation and palpation of the sharp front edge of the medial surface of the tibia. Further improvements can be made by optical or fluorescent alignment devices. For example, an optical mirror or a member of a defined light-fluorescent material could be strapped in a predetermined relation to the flat surface of the patient's leg over the tibia. A wire or wire mesh containing an x-ray or light fluorescent substance could similarly be adhered to the leg over the tibia. In either case, the x-ray source, or a source of substantially monochromatic light would be employed to irradiate the leg while the alignment of the instrument with respect to the leg were varied. A peak in the intensity of the fluorescent photons would indicate correct alignment of the leg to the instrument providing reproducible results. This arrangement could be readily employed in an automatic alignment embodiment of the instrument. Where generally within the skill of the art, such improvements are considered to be within the scope of the invention.

According to the applicants, studies on children, the typical thickness of the tissue over the tibia is 3 to 8 millimeters. Using a conventional x-ray source 20 with silver anode operated at 50 kV and 30 mA, a suitable exposure period is about 15 minutes. A typical area of radiation is 4 square centimeters.

A suitable x-ray source is available from the N.V. Philips Company of the Netherlands under their model number PW-1729/25. Improved sources are known to the art; these include x-ray lasers and synchrotron radiation sources. Certain of these devices provide polarized beams, such that the polarizer itself could be eliminated if these sources were employed. A Barkla polarizer suitable for use with the specified source can be made of a panel of Lucite (tm) or Rexolite (tm) plastic ¼ inch thick, which is readily available, disposed at 45° to the incident and polarized beams, as shown in FIG. 1. Other and more efficient polarizers are well known to the art.

A suitable Si(Li) detector 28 is available from the EG&G/Ortec Company of Oak Ridge, Tenn. under model number SLP-16220-8. The exact dimensions of the Si(Li) element can possibly be further optimized with respect to the geometry of the system and the frequency of the fluorescent photons to be detected; this may yield further improvements. As noted, the detector elements can also be increased in number to improve the signal-to-noise ratio.

The spectrum analyzer 30 and computer 32 are entirely conventional elements of laboratory equipment. Ultimately, it is envisioned that these and the other data processing components shown will be provided in a single simply controllable package which would also typically include controls for the x-ray source, means for recording data from a plurality of patients, and so forth.

The apparatus as described is capable of accurately measuring lead contents down to approximately 2 micrograms of lead per gram of bare bone (wet weight) and somewhat more for bone covered with soft tissue in vivo, typically between 4 and 8 micrograms of lead per gram of bone. Lead toxicity requiring treatment is indicated by measurements using the instrument of the invention at these levels. Further improvements in the apparatus, e.g., by improving the signal-to-noise ratio by increasing the irradiation flux density, either by employing higher intensity or polarized sources, by improving the efficiency of the polarization, or both, or by multiplying or improving the sensitivity of the detector(s), may allow direct measurement of lesser "elevated" skeletal lead levels, suggesting removal of the patient from lead sources.

Conveniently, the x-ray source, polarizer and detector can be mounted on a single machine element carried by a gantry providing sufficient range of movement to accommodate varying patients. The inventors have found it convenient to sit the patient in a chair with one leg outstretched in front, resting in a cradle. The x-ray source and the detector can then be brought close to the tibia, the detector at 90° to the source. Still more particularly, the x-ray fluorescence instrument of the invention can advantageously be built into a mobile van for use at factories, community screening centers, and the like.

Applicants have obtained substantial data corresponding to that shown in FIG. 2. Some of this data has been published; see "L-x-ray Fluorescence (XRF): a Rapid Assessment of Critical Bone Lead (Pb) in Pb-toxic Children," Rosen et al., *Pediatric Research,* 21, 287A (May 1987), Abstract 680. Applicants have also had abstracts accepted for the 1988 annual meeting of the Society of Toxicology, to occur in February 1988, and for the meeting of the American Pediatric Society, to take place in May 1988. These presentations will include further data. These publications clearly show the utility of applicants' claimed invention. The latter abstracts suggest that the complex EDTA chelation testing methodology described above will presently be replaced by a combination of blood lead testing and x-ray fluorescence testing according to this invention; EP pre-screening may also be employed, as noted.

While a preferred embodiment of the invention has been described in detail, it will be appreciated that numerous modifications and improvements thereto are within the skill of the art, and are accordingly considered to be within its scope. The invention is not to be limited by the above exemplary disclosure, but only by the following claims.

We claim:
1. Method for in vivo measurement of the skeletal lead burden in humans, comprising the steps of:
   irradiating a portion of bone with soft x-rays emitted by an x-ray tube having a silver anode;
   collecting photons fluoresced from atoms within said irradiated portion of bone;
   analyzing the energy spectrum of said collected photons to identify the atoms by which they were fluoresced;
   determining the amount of lead present in said bone as a result of said analyzing step.
2. The method of claim 1, comprising the further step of polarizing said radiation prior to irradiating said bone.
3. The method of claim 1 further comprising the step of displaying the spectra of the collected photons.
4. The method of claim 1, comprising the further steps of assessing the result of said analysis step with respect to the results of previous similar tests performed on patients having also had a EDTA chelation test for soft tissue and skeletal lead burden performed thereon, and using the result of said assessing step to prescribe chelation or other treatment for the patient.
5. Apparatus for in vivo measurement of the amount of lead in the skeleton of a patient, comprising:
   a source of soft x-rays, said source comprising an x-ray tube having a silver anode;
   means for disposing said source of soft x-rays with respect to said patient such that when energized it irradiates a portion of the bone of the patient with said soft x-rays;
   means for detecting photons emitted by atoms in said portions of bone irradiated by radiation from said source, and for generating an output signal responsive to the energies of individual ones of said emitted photons;
   means for analyzing the spectrum of said output signal responsive to the energies of ones of said photons emitted by said elements in response to said irradiation; and
   means responsive to said analyzed spectrum to determine the skeletal lead content of the patient.
6. The apparatus of claim 5, further comprising means for polarizing said radiation prior to irradiating the patient therewith.
7. The apparatus of claim 5, further comprising means for comparing the amount of skeletal lead, as determined by said means responsive to the analyzed spectrum of the emitted photons, with comparable data from similar tests performed on patients having also had an EDTA chelation test performed thereon
8. The apparatus of claim 5, in combination with means for maintaining the bone of the patient in a specified physical relation to said source of radiation and to said detector.
9. Method of in vivo diagnosis of lead toxicity in a patient, comprising the steps of:
   performing a blood lead test on said patient;
   comparing the result of said blood lead test to first and second threshold levels;
   if said result exceeds a first higher level, immediately treating said patient for lead toxicity; and
   if said result falls in a range between said first higher and second lower levels, performing an x-ray fluorescence test, comprising the steps of:
   irradiating a portion of a bone of said patient by exposure to a source of soft x-rays, said source comprising an x-ray tube having a silver anode;
   detecting photons having been fluoresced from atoms in said bone responsive to said irradiation step;
   analyzing photons emitted by said atoms with respect to their energy; and
   measuring the relative height of lead-characteristic peaks in the energy spectrum of the emitted photons.
10. The method of claim 9 further comprising the step of substantially polarizing the radiation from said source prior to irradiation of the patient.
11. The method of claim 9, comprising the further step of correlating the amount of fluoresced photons detected in a particular segment of the spectrum with comparable results of earlier tests performed on other patients having also had EDTA chelation tests for lead burden performed thereon.
12. The method of claim 11 wherein said bone of said patient is irradiated for a predetermined period of time, and comprising the further step of correlating the result of said analyzing step with comparable results from similar tests performed on other patients to determine the absolute amount of the corresponding atoms present in said bone of said patient.
13. The method of claim 11 comprising the further steps of measuring the thickness of the tissue overlying said bone and correcting said absolute amount responsive to said measurement.
14. The method of claim 9 comprising the further step of displaying the spectrum of the detected photons for analysis by an operator.

* * * * *